(12) United States Patent
Granelli

(10) Patent No.: US 9,872,962 B2
(45) Date of Patent: Jan. 23, 2018

(54) DUAL CHAMBER MIXING SYRINGES AND METHODS OF USING SAME

(71) Applicant: MERCK SHARP & DOHME CORP., Rahway, NJ (US)

(72) Inventor: Christopher J. Granelli, Chatham, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/654,016

(22) PCT Filed: Dec. 17, 2013

(86) PCT No.: PCT/US2013/075552
§ 371 (c)(1),
(2) Date: Jun. 19, 2015

(87) PCT Pub. No.: WO2014/099846
PCT Pub. Date: Jun. 26, 2014

(65) Prior Publication Data
US 2015/0343153 A1      Dec. 3, 2015

Related U.S. Application Data

(60) Provisional application No. 61/739,762, filed on Dec. 20, 2012.

(51) Int. Cl.
*A61M 5/315*      (2006.01)
*A61M 5/19*       (2006.01)
(Continued)

(52) U.S. Cl.
CPC ........ *A61M 5/31596* (2013.01); *A61M 5/002* (2013.01); *A61M 5/19* (2013.01);
(Continued)

(58) Field of Classification Search
CPC .... A61M 5/31596; A61M 5/002; A61M 5/19; A61M 5/178; A61M 5/2066;
(Continued)

(56) References Cited

U.S. PATENT DOCUMENTS

| 3,248,014 A | 4/1966 | Gill |
| 3,380,451 A | 4/1968 | Porter |

(Continued)

FOREIGN PATENT DOCUMENTS

| DE | 1566644 | 1/1970 |
| DE | 1961166 | 7/1970 |

(Continued)

OTHER PUBLICATIONS

Machine Translation of DE1566644—Two-chamber injection syringe has inner unconnected piston with non-return valve and piston retention device.

(Continued)

*Primary Examiner* — Bhisma Mehta
*Assistant Examiner* — Nilay Shah
(74) *Attorney, Agent, or Firm* — Gloria M. Fuentes; Li Su

(57) ABSTRACT

Provided are mixing syringes having two chambers defined by a pair of pistons located one above the other inside the syringe. Mixing of components separately stored in each of the two chambers occurs when a reversible valve occluding a bore in the distal piston near the discharge end is unseated by removing the retention sleeve and pressing the knob, and the proximal piston nearer the top of the syringe is moved axially toward the distal piston. Further movement of the proximal piston causes it to abut the distal piston resulting in the two pistons acting as one to dispel the now mixed components through the discharge end. Methods are provided for using the syringes for storage and mixing components; discharging the components from the syringe such (Continued)

as by administering the components to a patient in need thereof through a needle when the components are a medicament product.

17 Claims, 7 Drawing Sheets

(51) Int. Cl.
*A61M 5/00* (2006.01)
*A61M 5/34* (2006.01)
*A61M 5/28* (2006.01)
*A61M 5/24* (2006.01)
*A61M 5/20* (2006.01)
*A61M 3/00* (2006.01)
*A61M 5/31* (2006.01)

(52) U.S. Cl.
CPC ............... *A61M 5/34* (2013.01); *A61M 3/005* (2013.01); *A61M 5/2066* (2013.01); *A61M 5/2448* (2013.01); *A61M 5/284* (2013.01); *A61M 2005/3128* (2013.01); *A61M 2005/3139* (2013.01); *A61M 2005/31598* (2013.01)

(58) Field of Classification Search
CPC .. A61M 5/2448; A61M 5/284; A61M 5/3294; A61M 2005/3128; A61M 2005/3139; A61M 2005/31598; A61M 2005/2451; A61M 3/005
See application file for complete search history.

(56) References Cited

U.S. PATENT DOCUMENTS

| | | | |
|---|---|---|---|
| 3,682,174 A | | 8/1972 | Cohen |
| 4,673,395 A | * | 6/1987 | Phillips ............ A61M 5/19 604/191 |
| 5,286,257 A | | 2/1994 | Fischer |
| 5,380,281 A | | 1/1995 | Tomellini |
| 5,630,800 A | | 5/1997 | Blank |
| 7,101,354 B2 | | 9/2006 | Thorne |
| 7,951,108 B2 | | 5/2011 | Harper |
| 8,231,567 B2 | | 7/2012 | Tennican |
| 2011/0233079 A1 | * | 9/2011 | Macinnes ......... A61M 25/002 206/232 |

FOREIGN PATENT DOCUMENTS

| | | | |
|---|---|---|---|
| EP | 0112574 | 7/1984 | |
| EP | 0112574 A1 | * 7/1984 | ......... A61M 5/2429 |
| EP | 0974373 | 1/2000 | |

OTHER PUBLICATIONS

Machine Translation of DE1961166—Apparatus for substances to be mixed at the place of use.
Machine Translation of EP0112574—Pre-filled syringe with double compartment.

* cited by examiner

DUAL CHAMBER MIXING SYRINGES AND METHODS OF USING SAME

This application claims the benefit of U.S. Provisional Patent Application No. 61/739,762; filed Dec. 20, 2012; which is herein incorporated by reference in its entirety.

FIELD OF THE INVENTION

This specification relates to syringes and methods of their use. More specifically, this specification relates to dual-chamber mixing syringes and methods of their use.

BACKGROUND OF THE INVENTION

A number of products are stored in a two-component form, and mixed together to form the final product prior to use. For example, certain drugs are not liquid stable and are stored as a two-component product: such as a lyophilized component, and separately a liquid component for reconstituting the lyophilized component prior to delivery. These constraints can create issues regarding long-term storage of drug components, and timely and proper mixing and administration of the drug.

A number of devices and methods have been used to mix and/or deliver two-component drugs, such as lyophilized drugs that are reconstituted. One example is the Merck REDIPEN®. The present disclosure relates to novel devices and methods for storing, mixing, and/or administering two-component products, such as two-component drugs.

While certain novel features are shown and described below, some or all of which may be pointed out in the claims, the devices and methods of this disclosure are not intended to be limited to the details specified, since a person of ordinary skill in the relevant art will understand that various omissions, modifications, substitutions and changes in the forms and details of the illustrated embodiments and in their operation may be made without departing in any way from the spirit of the disclosure. No feature described herein is critical or essential unless it is expressly stated as being "critical" or "essential."

SUMMARY OF THE INVENTION

The present disclosure provides devices and methods for storing, mixing, delivering, and/or administering two-component products, such as two-component drugs.

In some embodiments, the devices are dual-chamber syringes including: a hollow body having a distal discharge end and a proximal piston-rod receiving end; a piston-rod extending into the hollow body through an opening in the piston-rod receiving end; an axially-bored first piston and a second piston, each piston is positioned inside the hollow body in fluid-tight, slidable engagement with the inner walls of the hollow body, wherein the first piston is positioned nearer the discharge end than the second piston, the first piston together with the inner walls and discharge end of the hollow body define a first, distal chamber, the second piston together with the first piston and inner walls of the hollow body define a second, proximal chamber, and the second piston is in actuating engagement with the piston rod such that the second piston moves axially toward the discharge end when the piston rod is depressed; and, the syringe also includes a valve for reversibly sealing the axial bore in the first piston. In further embodiments, the dual-chamber syringe also includes a biasing member, such as a spring, for maintaining separation between the first and second pistons and/or for biasing the valve in sealing engagement with the first piston to occlude the axial bore therein. In further and/or other embodiments, the valve is in actuating engagement with the piston rod such that the valve disengages from the first piston when the piston rod is depressed. In further and/or other embodiments, the first piston is actuated when the second piston engages with it as a result of the piston rod being depressed.

In some embodiments, the devices are kits comprising one or more of the dual-chamber syringes as described above and further herein. In some embodiments, the dual-chamber syringes are pre-loaded with a first component of a product in the first chamber of the syringe and a second component of the product in the second chamber of the syringe. In further embodiments, the product is a medicament, and the first component is a solid component of the medicament and the second component is a liquid component of the medicament. In some embodiments, the solid component is the lyophilized form of a medicament and the liquid component is a liquid for reconstituting the lyophilized form when the two components are mixed together. In some embodiments, the kits comprise packaging in which the dual-chamber syringes are provided. In further embodiments, the kids include instructions, warning labels or combinations thereof on or in the packaging.

In some embodiments, the methods are a method of preparing a dual-chamber, mixing syringe for delivery of a two-component product and the methods include: loading and/or storing a first component of a two-component product in a first distal chamber of a two-chamber syringe, and loading and/or storing a second component of the two-component product in a second, proximal chamber of the two-chamber syringe, wherein the first distal chamber is nearer the discharge end than the second proximal chamber, and further wherein the two-chamber syringe is as described above and/or further herein. For example, the two-chamber, mixing syringe includes: a hollow body having inner walls, a distal discharge end and a proximal piston-receiving end; a piston rod extending into the hollow body through an opening in the piston-rod receiving end; an axially-bored first piston in fluid-tight, slidable engagement with the inner walls of the hollow body, wherein the first piston together with the inner walls and discharge end define a first, distal chamber in the hollow body; a second piston in fluid-tight, slidable engagement with the inner walls of the hollow body and in actuating engagement with the piston rod such that the second piston moves axially toward the distal discharge end when the piston rod is depressed, wherein the second piston together with the first piston and the inner walls of the hollow body define a second, proximal chamber in the hollow body; and, a valve for reversibly sealing the axial bore in the first piston.

In some embodiments, the methods further comprise mixing the first component and the second component to form a product by: removing the retention sleeve, actuating the valve to move axially and unseal the axial bore of the first piston, and actuating the second piston to move axially causing the second component to move through the axial bore into the first chamber. In some embodiments, the method further comprises discharging the product from the syringe by: further depressing the piston rod resulting in the second piston engaging with the first piston and causing the first piston to move axially toward the discharge end and dispel the product through an opening in the discharge end. In further embodiments, the discharged product is a medicament and the method comprises administering the medicament by: discharging the product through a needle at the discharge end. In some embodiments, the valve is actuated simultaneously with the second piston. In some embodiments, the valve and the second piston are both in actuating engagement with the piston rod such that depressing the piston rod causes both the valve and the second piston to move axially toward the discharge end.

While the disclosure provides certain specific embodiments, the invention is not limited to those embodiments. For example, although the disclosure specifically discusses the applicability of the devices and methods to two-component drugs, the devices and methods are not limited to two-component drugs. For example, the devices and methods may also be applicable to other two-component products, such as epoxy glues. A person of ordinary skill will appreciate from the description herein that modifications can be made to the described embodiments and therefore that the specification is broader in scope than the described embodiments. All examples are therefore non-limiting.

BRIEF DESCRIPTIONS OF THE DRAWINGS

DETAILED DESCRIPTION

Figure 1:
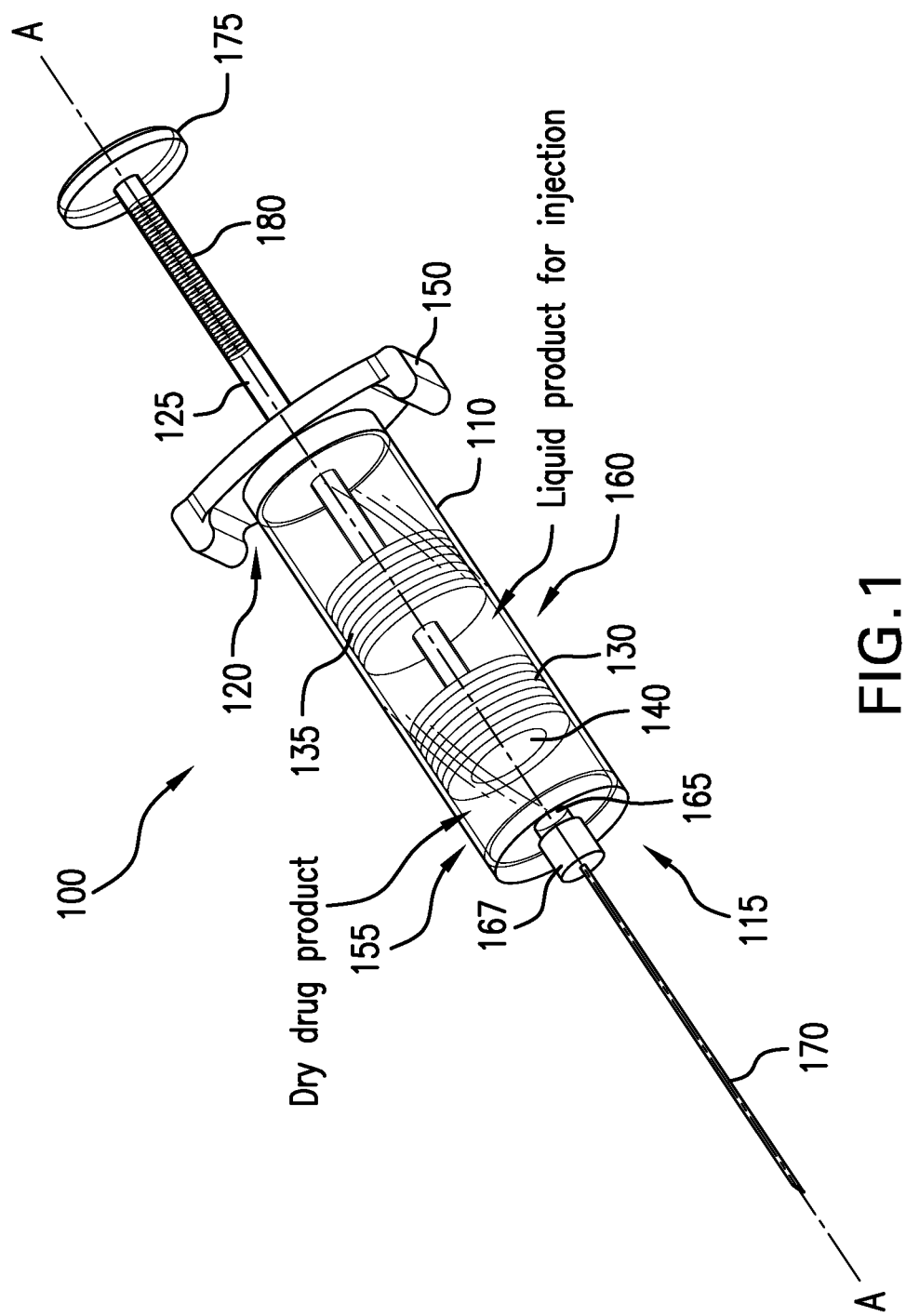
FIG. 1 is a schematic perspective view of an embodiment of a dual-chamber, mixing syringe in accordance with this disclosure prior to use.

Detailed descriptions of one or more embodiments are provided herein. It is to be understood, however, that the devices and methods according to this disclosure may be embodied in various forms. Therefore, specific details disclosed herein are not to be interpreted as limiting, but rather as a representative basis for the claims and for teaching one skilled in the art to employ the present devices and methods in any appropriate manner.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited. For example, "discharging the distal chamber" should be interpreted to mean "substantially discharging the distal chamber" because a person of skill should understand that it may not be possible to entirely remove the product from the distal chamber (for example, some residue may be left behind).

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

Where ever the terms "a" or "an" are used, "one or more" is understood unless explicitly stated otherwise or such interpretation is nonsensical in context.

The terms "connected," "attached," "affixed" or the like are understood to be modified by "directly or indirectly." In other words, if A is attached to B, it may be directly attached to B or indirectly attached to B through additional components. Similarly, "actuating engagement" and the like are understood to mean that if A is in actuating engagement with B, A may be directly actuated by B or indirectly actuated by B through additional components.

The disclosure provides devices and methods applicable for use with two-component products. In some embodiments, the devices and methods are useful for separately storing the components of the two-component product and also mixing together the components to form the product (for example, internally in the same device used to store the components), for example just prior to use. In further embodiments, the devices and methods are also useful for administration of the product, for example when the product is a drug. Generally, the devices are dual-chamber syringes that separately store two components of a product (one component in each chamber) until just prior to use, when the components are combined within the syringe and then delivered by actuation of the syringe.

Figure 2:
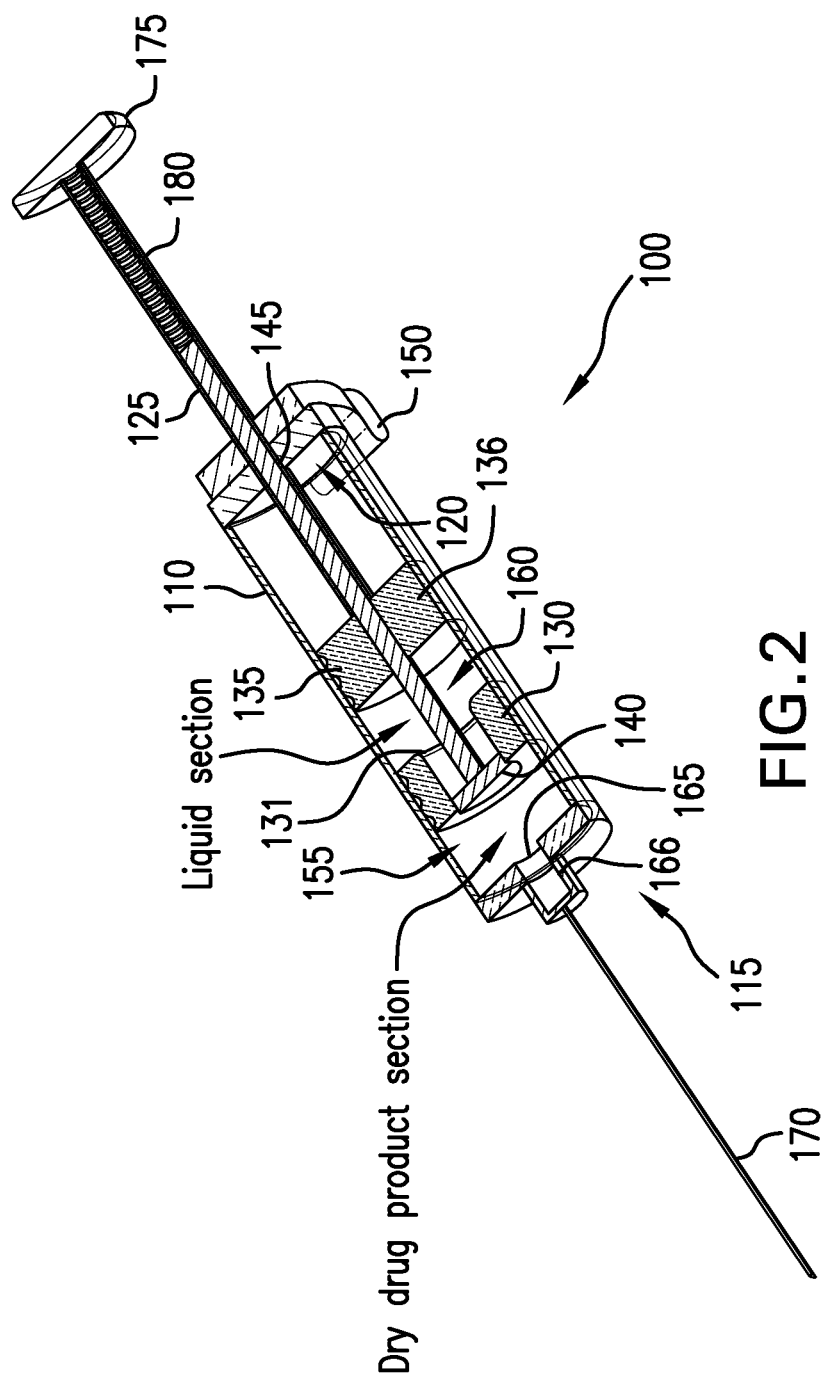
FIG. 2 is a cross-section schematic view of the syringe of FIG. 1, also illustrated prior to use, taken along the line A-A in FIG. 1.
Figure 3:
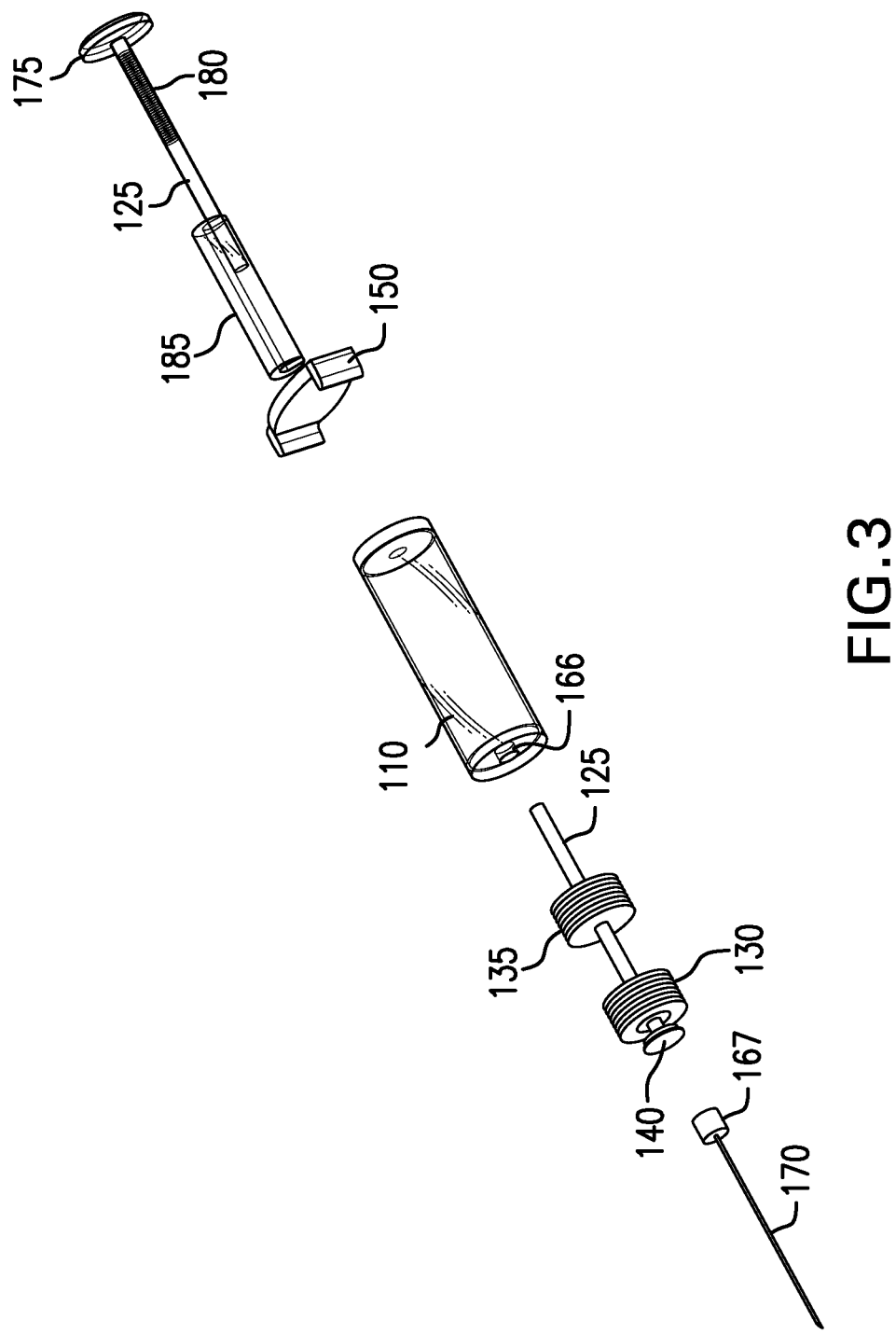
FIG. 3 is an exploded schematic perspective view of the syringe of FIG. 1, also illustrated prior to use.

Referring now to the Figures, wherein like reference numerals refer to like parts throughout, FIGS. 1-3 provide alternative views of the components of an embodiment of a dual-chamber, mixing syringe 100 according to this disclosure. FIG. 1 provides a schematic perspective view of the dual-chamber, mixing syringe 100, FIG. 2 provides a schematic, cross-section view of the dual-chamber, mixing syringe 100, and FIG. 3 provides an exploded, perspective view of the dual-chamber, mixing syringe 100 to better illustrate the various components of the syringe 100.

As is shown, the syringe 100 includes a housing 110 or hollow body, depicted as a hollow barrel, having a distal (discharge/delivery) end 115 and a proximal (piston-rod receiving) end 120. A person of skill understands that the syringe need not be barrel shaped. The distal end 115 has a discharge opening 165, which may be configured to removably mount a needle 170 (shown) in a manner that results in fluid communication between the needle lumen and interior of the hollow barrel 110. When the needle is removed, the discharge opening 165 may removably mount a closure element (not shown) to occlude the opening and prevent leakage of the component or product (if the components have been mixed) stored within the syringe 100. For example, the discharge opening 165 may have the form of an axially-bored projection or tip 166 (FIGS. 2 and 3), wherein the bore provides a fluid passage from one end of the tip to the other and therefore into the interior of the hollow barrel 110. The projection 166 may be threaded for interlocking engagement with a corresponding threaded, locking member 167 on a needle 170. The connection between the discharge opening 165 and the needle 170 and/or closure element, however, can be achieved by any means known in the art. In some embodiments, the needle 170 may be permanently mounted to the syringe 100.

The proximal end 120 of the hollow barrel 110 is closed off, but for a concentric opening 145 (FIG. 3) configured to receive a piston rod 125. In some embodiments, the piston rod 125 is fitted into the opening 145 to result in a fluid-tight, sliding engagement with the interior wall of the concentric opening 145 in the proximal end 120 of the hollow barrel 110. The piston rod 125 extends axially into the hollow barrel 110. The piston rod 125 may include a plunger knob 175 at its proximal end (or any other suitable device) to assist a user in depressing the piston rod 125 further into the hollow barrel 110. In some embodiments, the piston rod 125 may be comprised of multiple components. For example, the piston rod 125 may be a separate first piston rod and second piston rod, which may or may not have the same length and/or circumference. In embodiments wherein the piston rod 125 is a first piston rod and second piston rod, the first piston rod may extend through the pistons 130, 135, described in further detail below, and the second piston rod may be in actuating alignment with the first piston rod. For example, when the second piston rod moves axially toward the discharge end and engages with the first piston rod and/or the piston nearer the second piston rod, it causes the first piston rod to also move toward the discharge end.

In some embodiments, the housing 110 may be configured with a pair of flanges 150, which project outwardly from the hollow barrel 110. These flanges 150 provide a surface for an operator's fingers to grip during use. Other gripping devices (for embodiments including gripping devices) are within the scope of this disclosure.

The syringe 100 also includes a first, distal piston 130, a second, proximal piston 135, and a valve 140. The first, distal piston 130 is positioned nearer the discharge opening 165 than the second, proximal piston 135. And, each of the first, distal piston 130 and the second, proximal piston 135 form a fluid-tight seal with the interior wall of the hollow barrel 110. In this way, the hollow barrel 110 and the first, distal piston 130 together define a first, distal chamber 155 for housing a first component of a two-component product. Likewise, the hollow barrel 110, the first, distal piston 130 and the second, proximal piston 135 together define a second, proximal chamber 160 for housing the second component of a two-component product. The minimum (initial) size of each chamber 155, 160 is determined by the desired amount of each component, the volume that desired amount occupies, and in some embodiments, the volume the ultimate product may occupy, as well as the volume occupied by the piston rod 125.

In the illustrated embodiment, each of the first, distal piston 130 and the second, proximal piston 135 also include a central bore 131, 136 therethrough creating a fluid passage from one end of each piston 130, 135 to the other end of each piston 130, 135. The valve 140 is in releasable engagement with the first, distal piston 130 and is sized to occlude the central bore 131 of the first, distal piston 130 when in engaged with that piston 130. The central bore 131 of the first, distal piston 130 has a larger diameter than that of the piston rod 125 such that the central bore 131 of the first, distal piston 130 provides fluid communication between the second, proximal chamber 160 and the first, distal chamber 155 when the valve 140 disengages from the first, distal piston 130, even when the piston rod 125 is disposed in the first piston's 130 central bore 131. By contrast, the second, proximal piston's 135 central bore 136 is sized to create a fluid-tight seal between the second, proximal piston 135 and the piston rod 125.

Each of the pistons 130, 135, despite forming a fluid-tight seal with the interior wall of the hollow barrel 110, are also in slidable engagement with the interior wall of the hollow barrel 110. Consequently, because the second, proximal piston 135 is fixedly attached to the piston rod 125, as described above, whereas the first, distal piston 130 is not, when a user removes the retention sleeve depresses the piston rod causing it to move further into the hollow barrel 110 toward the discharge opening 165, the movement of the piston rod also actuates the second, proximal piston 135 causing it also to move axially within the hollow barrel 110 toward the discharge opening 165. By contrast, the first, distal piston 130 remains stationary until the second, proximal piston 135 engages with it. Once the second, proximal piston abuts the first, distal piston, further depressing the piston rod 125 creates a force that is translated from the second, proximal piston 135 to the first, distal piston 130 resulting in the first, distal piston 130 also moving axially within the hollow barrel 110 toward the discharge opening 165. In some embodiments, depressing the piston rod 125, in addition to actuating the second, proximal piston 135, also actuates the valve 140 and causes it to disengage from the first, distal piston 130 creating fluid communication between the second, proximal chamber 160 and the first, distal chamber 155.

In some embodiments, the syringe 100 also includes a biasing member 180 that provides resistance when the piston rod is depressed. In the embodiment shown, the biasing member 180 is a spring wrapped around at least a portion of the piston rod 125 positioned outside the hollow barrel 110. In some embodiments, the biasing member 180 therefore maintains separation between the first and second pistons 130, 135 (i.e. provides resistance when the piston rod is depressed and the spring engages with the plunger knob 175 and proximal end 120 of the hollow body 110). In some embodiments, the biasing member 180 may also maintain separation between the first and second pistons 130, 135 when the syringe 100 is not in use. In some embodiments, the valve 140 is rigidly fixed to the piston rod 125 and the biasing member 180 may also provide a force that maintains the valve 140 in sealing engagement with the first, distal piston 130 when the syringe is not in use.

In some embodiments, the syringe 100 further includes a retention member 185 (shown in FIG. 3). The retention member or sleeve 185 prevents or alleviates slippage of the piston rod 125 when the syringe 100 is not in use, to prevent or alleviate premature, unwanted movement of the one or more of the pistons 130, 135 and/or valve 140. In some embodiments, the retention member or sleeve 185 may be a removable sleeve, which is disengaged from the syringe 100, for example at the time of use. However, the retention member or sleeve 185 is not limited to a sleeve, and may be any component known in the art or that may be envisaged for accomplished the goal of preventing or alleviating unwanted movement of the pistons and/or valve when the syringe is not in use.

FIGS. 1, 2 and 4-7 together illustrate operation of the dual-chamber, mixing syringe 100. FIG. 2 illustrates the syringe 100 prior to use, in its "rest" position. As shown, the valve 140 is seated in a sealed engagement with the first, distal piston 130 and the first distal piston 130 and second, proximal piston 135 are positioned within the hollow barrel 110 to define a first, distal chamber 155 for housing a first component (not shown) of a two-component product and a second, proximal chamber 160 for housing a second component (not shown) of a two-component product.

Figure 4:
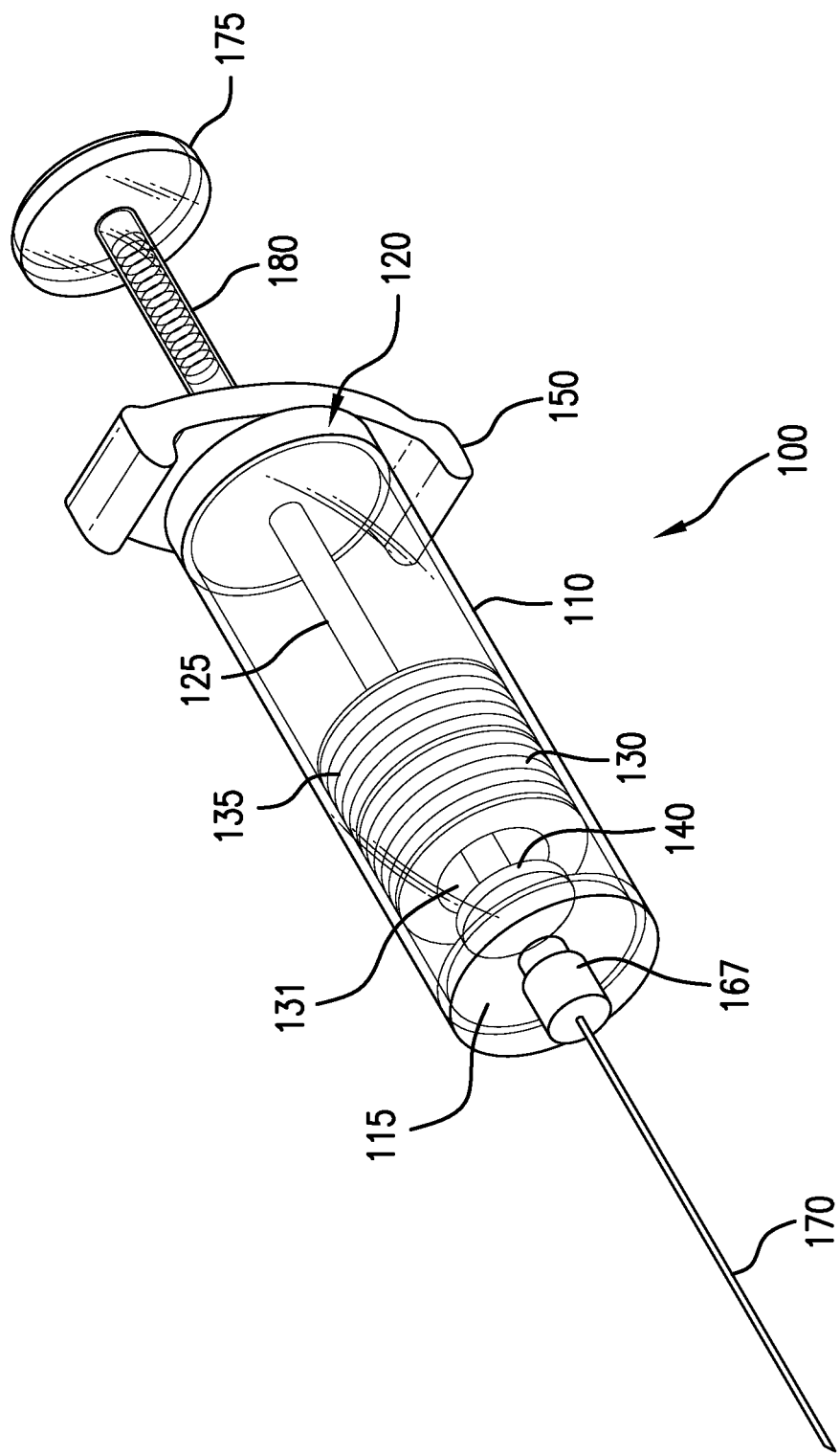
FIG. 4 is a schematic perspective view of the syringe of FIG. 1 after the proximal chamber has been evacuated.
Figure 5:
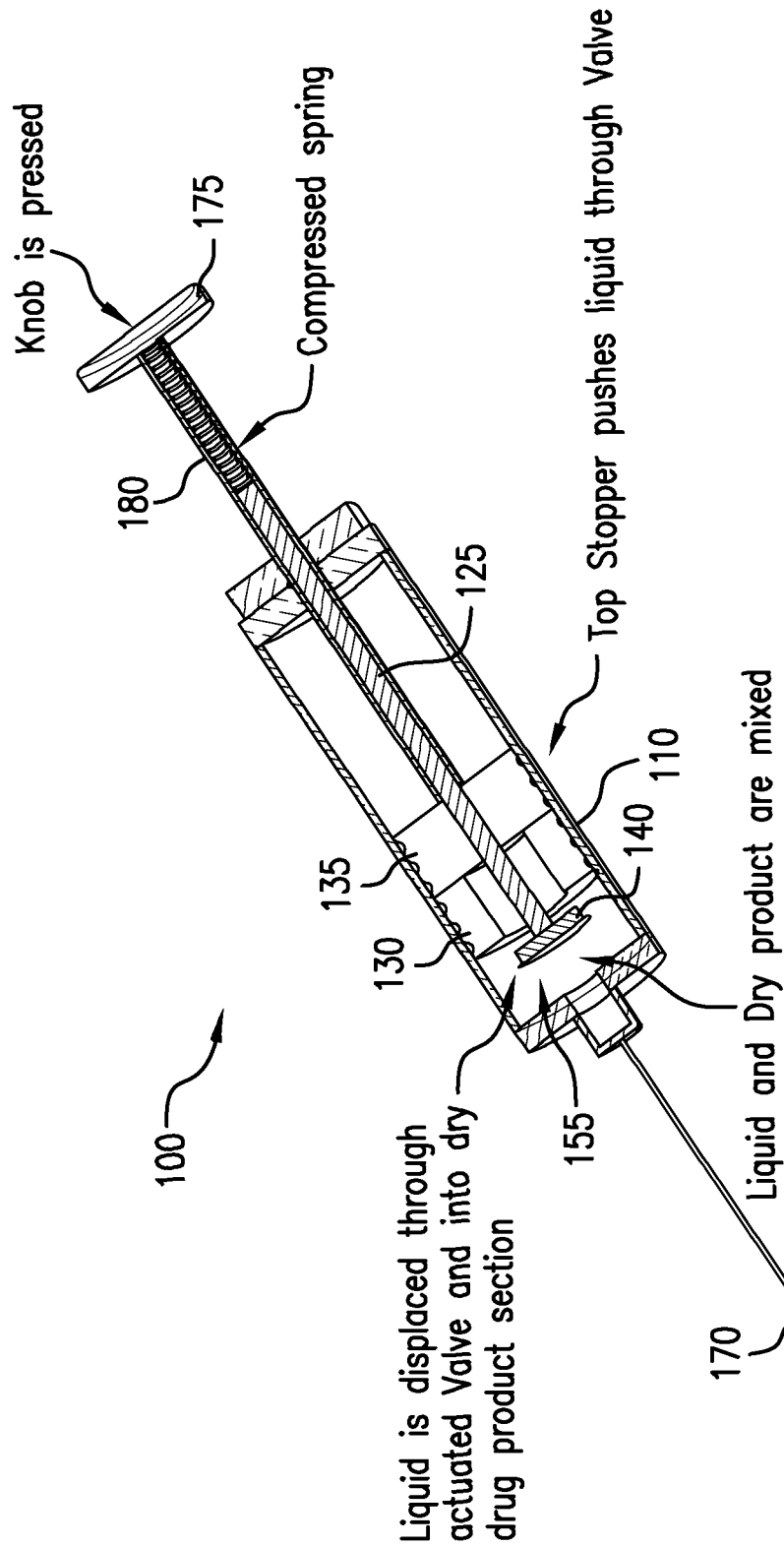
FIG. 5 is a cross-section schematic view of the syringe of FIG. 1, taken along the line B-B in FIG. 4, after the proximal chamber has been evacuated.
Figure 6:
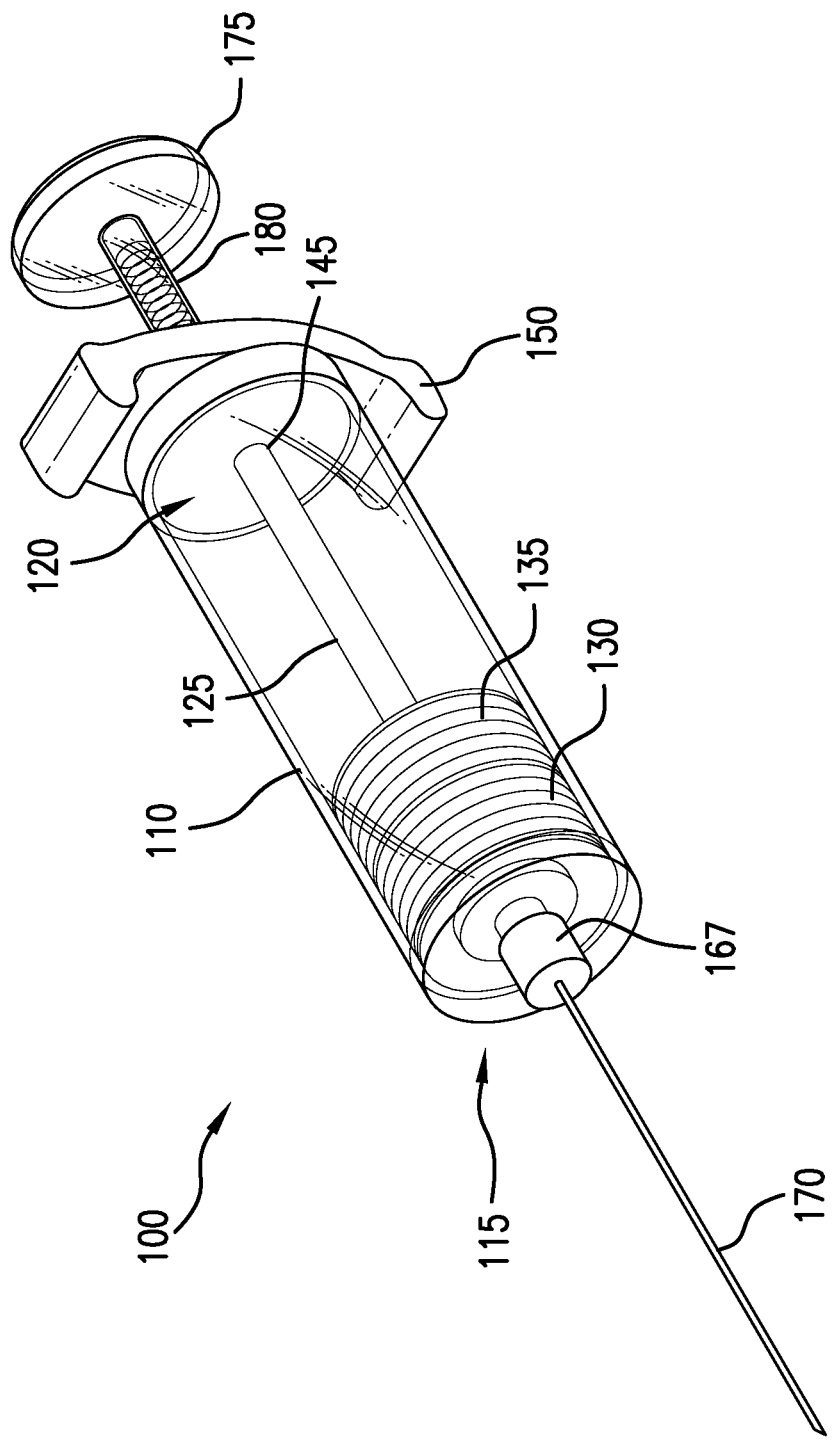
FIG. 6 is a schematic perspective view of the syringe of FIG. 1 after the distal chamber has been evacuated and the product has been discharged.
Figure 7:
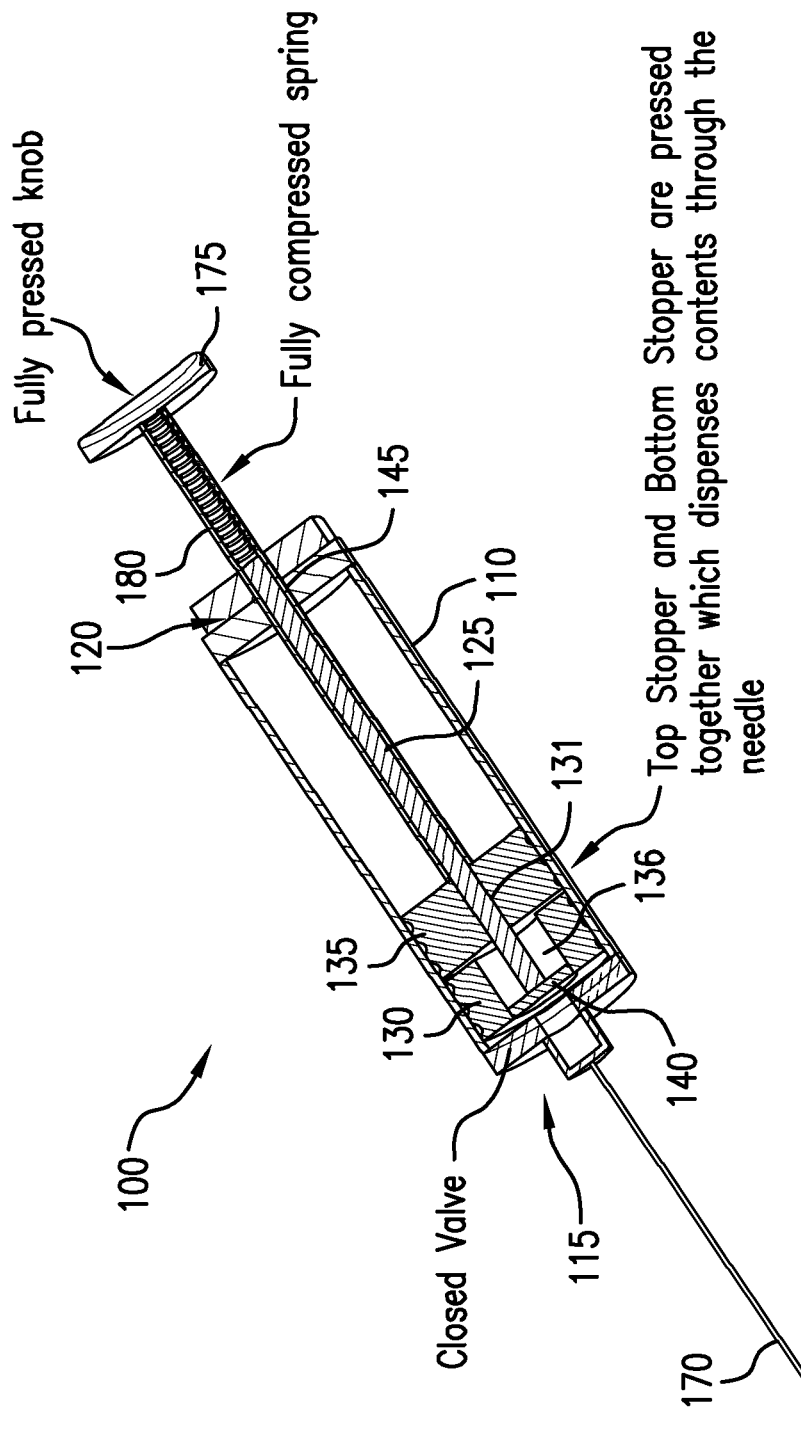
FIG. 7 is a cross-section schematic view of the syringe of FIG. 1, taken along the line C-C in FIG. 6, after the distal chamber has been evacuated and the product has been discharged.

As shown in FIGS. 4 and 5, in operation, a user depresses the piston rod 125 actuating both the valve 140 and the second, proximal piston 135 to move axially toward the discharge opening 165. Axial movement of the valve 140 unseats it from the first, distal piston 130 opening a fluid passage (the axial bore in the first, distal piston) between the first, distal chamber 155 and the second, proximal chamber 160. At the same time, axial movement of the second, proximal piston 135 forces the second component through the fluid passage and into the first, distal chamber 155, ultimately evacuating the second component from the second, proximal chamber 165 when the second, distal piston 135 has moved into engagement with the first, distal piston 130. Transfer of the second component from the second, proximal chamber 160 to the first, distal chamber 155 results in the first component and second component mixing with one another to form the product. As shown in FIGS. 6 and 7, continuing to depress the piston rod 125 causes the first and second pistons 130, 135 to act as a unitary piston, which forces the product through the discharge opening 165 and needle 170.

The present disclosure also provides kits comprising one or more dual-chamber, mixing syringes which are pre-loaded with a first and second component for making a product. The first and second components are stored separately in the first and second chambers respectively.

The product may potentially be any two-component product such as a lyophilized (freeze-dried) drug product and a liquid diluent for reconstituting the drug product prior to parenteral administration. Dual chamber mixing syringes are especially beneficial for products administered in settings where the absence of a cold chain compromises the stability and quality of the drug product, or in home care settings where patients are required to self-administer drugs for chronic conditions. Many new drugs, especially those developed by bio-pharmaceutical companies, are initially marketed in lyophilized form for two primary reasons: shelf-life and time-to-market. A lyophilized drug maintains its stability and potency over time, extending its shelf-life for prolonged storage. Many biologic drugs are also unable to be prefilled into a liquid-stable format due to their molecular complexity. As a result, an increasing number of novel drugs and vaccines are now being approved by regulatory agencies in a lyophilised format for reconstitution at the point of delivery. Some pharmaceutical companies are also developing injectable therapies that require mixing of two liquid-stable drugs at the point of delivery. As the number of lyophilized drug products that are marketed in emerging market countries or developed for self-administration increases, so too does the need for systems and devices to administer them. Furthermore, the active drug product may be manufactured and marketed in solid form, liquid form, or combinations thereof (such as an emulsion or colloidal suspension). And, the product may include one or more compounds. Consequently, each of the first component and second component may be in solid form, liquid form, or combinations thereof, and may include one or more compounds.

In some embodiments, the product is a two-component medicament, such as a first, solid component and a second, liquid component (for example, liquid carrier) for mixing with the solid component, for example for ease of ultimate administration of the drug. In some embodiments, the solid component is a lyophilized drug, and the liquid component is for reconstituting the lyophilized, solid component into liquid form. In some embodiments, the pre-loaded syringes are provided with the solid component loaded in the first, distal chamber (nearer the discharge end) and the liquid component loaded in the second, proximal chamber (nearer the piston-rod receiving end). In some such embodiments, when an operator actuates the piston rod, the valve sealing the first distal, piston (e.g. occluding the axial bore in the first, distal piston) disengages from the first, distal piston creating fluid communication between the first, distal chamber and the second, proximal chamber. In some embodiments, actuation of the piston rod also results in the second, distal piston moving axially toward the first, distal piston causing the second component (for example the liquid) to flow into the first, distal chamber and mix with the first component (for example the solid).

In some embodiments, the medicament is oxytocin and the kits comprise one or more syringes with a lyophilized, solid form of oxytocin pre-loaded into the first, distal chamber, and a liquid for reconstituting or carrying the oxytocin pre-loaded into the second, proximal chamber. Other non-limiting examples of medicaments to which the devices and methods of this disclosure are applicable include: biologic and biosimilar products, including but not limited to antibodies, fusion proteins, proteins, peptides, vaccines, hormones, and antithrombotics.

The syringe and its components may be made from any suitable materials known in the art, by any suitable means known in the art. In addition, the syringe may be pre-loaded by any means known in the art. For example, the pistons may be made from an elastomeric material, and the housing, piston rod and valve may be manufactured from a plastic material, for example by an injection molding process. In some embodiments, the housing including its end caps is a unitary piece, and in some embodiments, the housing may comprise two or more components such as a hollow tube and independent end caps (one having a discharge opening, and the other having an opening configured to receive the piston rod). In some embodiments, the internal components of the syringe, including the first and second component are assembled to insure sterility according to methods known in the art.

The present disclosure also provides methods of preparing a dual chamber, mixing syringe for administering a two-component product, for example, a two-component medicament. In some embodiments, the methods of preparing the syringe comprise: providing a first component of a two-component product in a first, distal chamber of a two-chamber syringe (such as loading a lyophilized, solid form of a drug into the first, distal chamber); and, providing a second component of the two-component product in a second, proximal chamber of the two-chamber syringe (such as loading a liquid carrier or liquid for reconstituting the lyophilized form of the drug into the second, proximal chamber), wherein the two-chamber syringe is as described herein.

Methods according to this disclosure also include methods for preparing and a two-component product in the syringe and discharging the two-component product from the syringe, such as a preparing a two-component medicament in the syringe and/or discharging the two-component medicament from the syringe. In some embodiments, the methods comprise actuating the valve of a two-chamber syringe (as described herein) having a first component of a two-component product in one chamber, and a second-component of a two-component product in another chamber in order to open a fluid passage between the first chamber and the second chamber resulting in the second component flowing out of the second chamber into the first chamber and mixing with the first component. In some embodiments, in addition to actuating the valve, a piston is also actuated (for example simultaneously with the valve) inside the two-chamber syringe, which provides a force for dispelling the second component from the second chamber into the first chamber to mix with the first component and form the product. For example, actuating the piston rod of a syringe may cause simultaneous axial movement of the valve opening up a fluid path between the first and second chamber and also axial movement of a "second" piston (e.g. the "second" piston defines the top of the second chamber). In some embodiments, the piston travels axially toward the first chamber, reducing the size of the second chamber (while maintaining the size of the first chamber) until it abuts the top of the first chamber. Axial movement of this piston forces the component in the proximal chamber to discharge into the distal chamber, mixing with the component in the distal chamber and forming product. In some embodiments, further actuation of the piston rod results in discharging the product from the syringe. For example, further actuation of the piston rod causes the same piston to push against another piston (defining the top of the first chamber), such that the two pistons act as one, move together axially toward the discharge end, reducing the size of the first chamber and forcing the product to dispel through an opening in the discharge end, or for example through a tip or a needle at the discharge end.

In some embodiments, the methods further comprise administering the product, for example administering the drug. The methods comprise dispelling the product through a needle at the discharge end of the syringe and administering the drug. Any suitable method of administration can be employed, for example the product (mixed composition) can be administered to a patient by intravenous, intramuscular, intraperitoneal, or subcutaneous routes.

In the above-described method embodiments, the two-chamber, mixing syringe may comprise: a hollow barrel having a distal discharge end and a proximal piston-rod receiving end; a piston rod extending into the hollow barrel through an opening in the piston-rod receiving end; an axially-bored first piston and a second piston, each in slidable and fluid-tight engagement with the hollow barrel, wherein the first piston is nearer the distal, discharge end than the second piston such that the walls of the hollow barrel, the discharge end of the hollow barrel and the first, distal piston define the first chamber (the discharge end defining the bottom of the first chamber and the first, distal piston defining the top of the first chamber), and the walls of the hollow barrel and the first, distal piston and the second distal piston define the second chamber (the first, distal piston defines the bottom of the second chamber and the second, distal piston defines the top of the second chamber). In addition, only the second piston is fixedly attached to the piston rod such that movement of the piston rod directly results in movement of the second piston but not the first piston. The dual-chamber syringe also comprises a valve for reversibly sealing the axial bore in the first piston (e.g. occluding the axial bore in the first piston), wherein when the valve is engaged with the axial bore it maintains separation between the chambers and when the valve is disengaged from the first piston, a fluid passage is opened up between the chambers, permitting the second component to flow through the axial bore from the second chamber to the first chamber and mix with the first component. In some embodiments, actuation of the piston rod causes the valve to disengage from the first piston.

A number of embodiments have been described but a person of skill understands that still other embodiments are encompassed by this disclosure. It will be appreciated by those skilled in the art that changes could be made to the embodiments described above without departing from the broad inventive concepts thereof. It is understood, therefore, that this disclosure and the inventive concepts are not limited to the particular embodiments disclosed, but are intended to cover modifications within the spirit and scope of the inventive concepts including as defined in the appended claims. Accordingly, the foregoing description of various embodiments does not necessarily imply exclusion. For example, "some" embodiments or "other" embodiments may include all or part of "some", "other," "further," and "certain" embodiments within the scope of this invention.

What is claimed is:

1. A dual-chamber, mixing syringe, comprising:
 a. a hollow body having inner walls, a distal discharge end, and a proximal piston-rod receiving end;
 b. a piston rod extending into the hollow body through an opening in the piston-rod receiving end;
 c. an axially-bored first piston and a second piston, wherein each piston is positioned inside the hollow body in slidable, fluid-tight engagement with the inner walls of the hollow body, wherein:
  i. the first piston is positioned nearer the discharge end than the second piston;
  ii. the first piston together with the inner walls of the hollow body and the discharge end of the hollow body define a distal chamber;
  iii. the second piston together with the first piston and the inner walls of the hollow body define a proximal chamber; and,
  iv. the second piston is in actuating engagement with the piston rod such that the second piston moves axially toward the discharge end when the piston rod is depressed; and,
 d. a valve rigidly affixed to the piston rod, such that the valve disengages from the first piston when the piston rod is depressed for reversibly sealing the axial bore in the first piston.

2. The dual-chamber, mixing syringe according to claim 1, further comprising a biasing member configured to maintain separation between the first and second pistons.

3. The dual-chamber, mixing syringe according to claim 2, wherein the biasing member is a spring wrapped around a portion of the piston rod extending outside the piston-rod receiving end of the hollow body.

4. The dual-chamber, mixing syringe according to claim 2, wherein the biasing member also biases the valve in sealing engagement with the axial bore of the first piston.

5. The dual-chamber, mixing syringe according to claim 1, further comprising gripping flanges on the hollow body.

6. The dual-chamber, mixing syringe according to claim 1, wherein the first piston is actuated to move axially toward the discharge end when the second piston engages with the first piston as a result of the piston rod being depressed.

7. The dual-chamber, mixing syringe according to claim 1, wherein a solid component of a medicament product is in the distal chamber, and a liquid component of the medicament product is in the proximal chamber.

8. The dual-chamber, mixing syringe according to claim 7, wherein when the piston rod is initially depressed, the second piston and the valve move axially toward the discharge end of the hollow body creating a fluid passage between the distal chamber and the proximal chamber through the axial bore of the first piston, and causing the liquid in the proximal chamber to flow into the distal chamber through the fluid passage and mix with the solid to form the medicament product; and continuing to depress the piston rod results in the second piston engaging with the first piston, causing the first piston to move axially together with the second piston toward the discharge end and the medicament product to be delivered through the discharge end.

9. A method for preparing a dual-chamber, mixing syringe of claim 1 for delivery of a two-component product, comprising:
  a. providing a first component of a two-component product in the distal chamber of the syringe; and,
  b. providing a second component of the two-component product in the proximal chamber of the syringe.

10. The method according to claim 9, further comprising: mixing the first and second component to form the two-component product by: actuating the valve to move axially and unseal the axial bore of the first piston, and actuating the second piston to move axially causing the second component to move through the axial bore into the distal chamber.

11. The method according to claim 10, wherein the two-component product is a medicament, the first component is a solid and the second component is a liquid, and the method further comprises administering the medicament by: further depressing the piston rod resulting in the second piston engaging the first piston and causing the first piston to move axially toward the distal discharge end and dispel the product through a needle attached to the discharge end.

12. The method according to claim 11, wherein the valve is in actuating engagement with the piston rod such that depressing the piston rod causes axial movement of the second piston and the valve.

13. The method according to claim 12, wherein the piston rod causes substantially simultaneous axial movement of the second piston and the valve when the piston rod is depressed.

14. The method according to claim 11, wherein the syringe further comprises a biasing member configured to maintain separation of the distal and proximal chamber and bias the valve in sealed engagement with the axial bore of the first piston.

15. A kit comprising one or more dual-chambered, mixing medical syringes of claim 1 for delivering a two-component medication, wherein the one or more medical syringes contain a first component of a medicament in the distal chamber of the syringe and a second component of the medicament in the proximal chamber of the syringe.

16. The kit according to claim 15, wherein the kit further comprises packaging into which one or more of the dual-chambered medical syringes is placed.

17. The kit according to claim 16, further comprising instructions, warning labels, and combinations thereof in or on the packaging.

* * * * *